United States Patent
Brodnick et al.

(10) Patent No.: US 7,787,952 B2
(45) Date of Patent: Aug. 31, 2010

(54) DETECTION OF FUNCTION OF IMPLANTED MEDICAL DEVICES

(75) Inventors: Donald E. Brodnick, Cedarburg, WI (US); David G. Hernke, Sussex, WI (US); Brian J. Young, Germantown, WI (US); David E. Albert, Oklahoma City, OK (US); Robert T. Wolfe, Elm Grove, WI (US); James M. Gray, Fox Point, WI (US); Paul S. Schluter, Whitefish Bay, WI (US)

(73) Assignee: The General Electric Company, Schenectady, NY (US)

( * ) Notice: Subject to any disclaimer, the term of this patent is extended or adjusted under 35 U.S.C. 154(b) by 524 days.

(21) Appl. No.: 11/933,863

(22) Filed: Nov. 1, 2007

(65) Prior Publication Data
US 2008/0051846 A1 Feb. 28, 2008

Related U.S. Application Data

(62) Division of application No. 10/685,810, filed on Oct. 15, 2003, now Pat. No. 7,315,760.

(51) Int. Cl.
*A61N 1/00* (2006.01)
(52) U.S. Cl. ..................................................... 607/28
(58) Field of Classification Search ............... 607/2, 607/5, 9, 27–31, 601; 128/901
See application file for complete search history.

(56) References Cited

U.S. PATENT DOCUMENTS

| 6,216,038 B1 * | 4/2001 | Hartlaub et al. ............... 607/31 |
| 6,450,172 B1 | 9/2002 | Hartlaub et al. |
| 6,453,201 B1 | 9/2002 | Daum et al. |
| 6,458,086 B1 | 10/2002 | Franco et al. |
| 6,468,219 B1 | 10/2002 | Njemanze |
| 6,468,263 B1 | 10/2002 | Fischell et al. |
| 6,471,645 B1 | 10/2002 | Warkentin et al. |
| 6,497,655 B1 | 12/2002 | Linberg et al. |
| 6,501,983 B1 | 12/2002 | Natarajan et al. |
| 6,539,253 B2 | 3/2003 | Thompson et al. |
| 2002/0137991 A1 | 9/2002 | Scarantino et al. |
| 2002/0138009 A1 | 9/2002 | Brockway et al. |
| 2002/0143371 A1 | 10/2002 | Balczewski et al. |
| 2002/0193847 A1 | 12/2002 | Daum et al. |
| 2003/0045908 A1 | 3/2003 | Condie et al. |

FOREIGN PATENT DOCUMENTS

| WO | WO 02/074386 | 9/2002 |
| WO | WO02/087696 | 11/2002 |

* cited by examiner

*Primary Examiner*—George Manuel
(74) *Attorney, Agent, or Firm*—Andrus, Sceales, Starke & Sawall, LLP

(57) ABSTRACT

A monitoring system and method for monitoring signals from an implantable medical device are disclosed. The monitoring system and method include a monitor configured to detect a radio frequency artifact from the signals of the implantable medical device and circuitry for processing the radio frequency artifact from the signals of the implantable medical device.

17 Claims, 4 Drawing Sheets

US 7,787,952 B2

DETECTION OF FUNCTION OF IMPLANTED MEDICAL DEVICES

CROSS-REFERENCE TO RELATED APPLICATIONS

This application is a divisional of application Ser. No. 10/685,810 filed Oct. 15, 2003, now U.S. Pat. No. 7,315,760.

BACKGROUND

The present invention relates generally to the field of implanted medical devices. More particularly, the invention relates to the detection of pacing stimulus artifacts from implanted electronic pacemakers.

Detection of pacing stimulus artifacts from implanted electronic pacemakers in the body surface electrocardiogram (ECG) is sometimes difficult due to sophisticated and more evolved generations of implanted devices that stimulate the heart muscle. In addition, artifacts in the body surface ECG have gotten smaller and/or more complicated in shape and sequence. Further, pacemakers and cardio defibrillators emit their own diagnostic signals which can sometimes confuse circuits.

Accordingly, there exists a need for improved detection of pacing stimulus artifacts from implanted pacemakers. Further, there exists a need for improved detection/recognition of small pacer stimuli and improved rejection of large pacer stimuli to increase reliability of the critical functions of cardiac monitors and electrocardiographs. Further, there exists a need for the detection of artifacts regardless of which manufacturer has made the implanted pacer and regardless of which version of firmware or communications protocol is in the pacer.

SUMMARY

One embodiment of the invention relates to a monitoring system comprising an implantable medical device configured to be implanted in a patient to provide a stimulus to the patient and a monitor having processing circuitry configured to detect a radio frequency artifact from the stimulus of the implantable medical device in order to eliminate an occurrence of falsely identifying voltage artifact as a heart beat.

Another embodiment of the invention relates to a monitoring system comprising a monitor configured to detect a radio frequency artifact from the signals of an implantable medical device and processing circuitry configured to process the radio frequency artifact from signals of the implantable medical device in order to determine where artifact occurs in an ECG and identify heart beats that are paced and heart beats that are not paced and occurrences of pacing that fail to stimulate a heart beat.

Another embodiment of the invention relates to a circuit for processing voltage artifact from implantable pacemaker signals comprising a slew limit circuit to limit pace artifact energy in the signals and a tunable band pass filter operable in parallel to the slew limit circuit and configured to isolate the voltage artifact from ambient noise and heart signals.

Another embodiment of the invention relates to a method of monitoring signals from an implantable medical device that provides a stimulus to a patient comprising detecting a radio frequency artifact from the implantable medical device and processing the radio frequency artifact from the implantable medical device in order to determine where artifact occurs in an ECG and identify heartbeats that are paced and heartbeats that are not paced and occurrences of pacing that fail to stimulate a heart beat.

Another embodiment of the invention relates to a system for monitoring signals from an implantable medical device comprising a means for detecting a radio frequency artifact from the implantable medical device and a means for processing the radio frequency artifact from the implantable medical device in order to determine where artifact occurs in an ECG and identify heart beats that are paced and heart beats that are not paced and occurrences of pacing that fail to stimulate a heart beat. The voltage artifact is excluded from heart rate determinations.

Another embodiment of the invention relates to a method for monitoring a signal from an implantable medical device comprising filtering voltage samples from multiple channels of the signal, detecting at least one of a leading edge and a trailing edge for a pulse, measuring width of a pulse, measuring amplitude of the pulse, validating the pulse, classifying the pulse, and storing information about the pulse.

Another embodiment of the present invention relates to a system for monitoring a signal from an implantable medical device comprising a means for filtering voltage samples from multiple channels of the signal, a means for detecting at least one of a leading edge and a trailing edge for a sample, a means for measuring width of a pulse, a means for measuring amplitude of the pulse, a means for validating the pulse, a means for classifying the pulse, and a means for storing information about the pulse.

Another embodiment of the present invention relates to a monitoring method comprising detecting a radio frequency artifact from signals of an implantable pacemaker, processing the radio frequency artifact from the signals of the implantable pacemaker, determining where radio frequency artifact occurs in an ECG, identifying heart beats that are paced and heart beats that are not paced and occurrences of pacing that fail to stimulate a heart beat, and excluding voltage artifact from a heart rate determination.

DETAILED DESCRIPTION OF EXEMPLARY EMBODIMENTS

Figure 1:
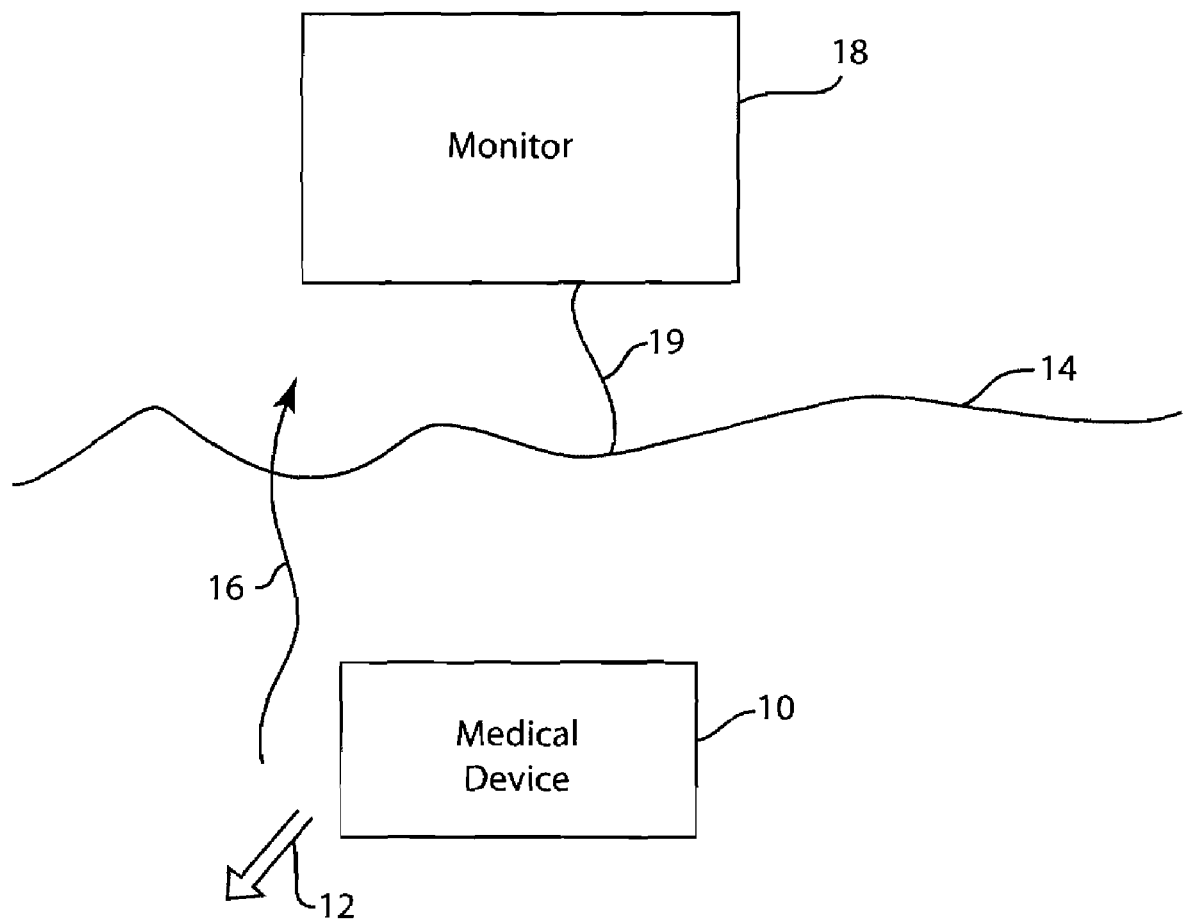
FIG. 1 is an illustration of an implantable medical device implanted in a patient in conjunction with an external monitor according to an exemplary embodiment.

Referring to FIG. 1, implantable medical device 10 provides an output 12 to a patient 14. According to an exemplary embodiment, the output includes an intended stimulus provided to patient 14. According to various embodiments, output 12 may include electrical pacing signals supplied by a pacemaker, electrical defibrillation signals, etc. Output 12 may also include incidental output signals. For example, output 12 may include a radio frequency signal (RF) 16.

A monitor 18 as shown in FIG. 1 is externally attached adjacent to or relatively near the body of patient 14. According to a preferred embodiment, monitor 18 is attached in a position on the body of patient 14 in relatively close proximity to output 12.

According to an exemplary embodiment, monitor 18 monitors signals from implantable medical device 10. According to a preferred embodiment, monitor 18 monitors and detects radio frequency (RF) artifact coincident with output 12 (e.g., pacemaker stimulus). Oftentimes, the current flow in the implanted pacing lead wires is short duration and generally unshielded so that an RF artifact may be detectable by monitor 18 comprising an antenna 19 placed on (or very near) a patient's body surface over the implanted pacemaker. The antenna 19 is preferably integrated into an existing lead wire such as an ECG electrode. The antenna may be designed to be responsive to the electric field, the magnetic field, or both. According to various alternative embodiments, monitor 18 may also detect other types of unintentional output artifacts from implantable medical device 10 such as a magnetic field, an electrical field, an acoustic sound, etc.

Figure 2:
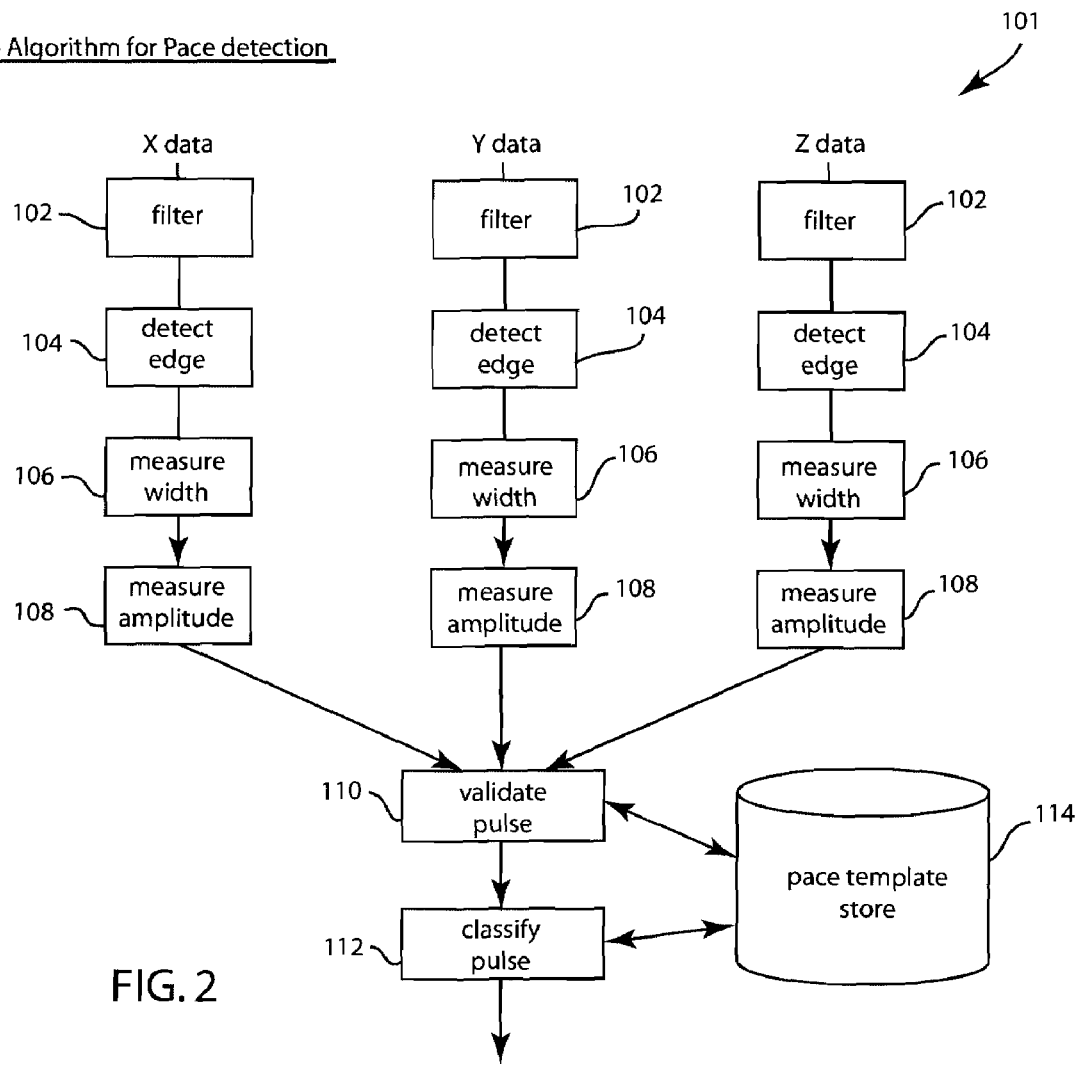
FIG. 2 is a schematic representation of a software algorithm for pace detection according to an exemplary embodiment.

According to an exemplary embodiment, the improvements to the detection of pacing stimulus artifacts from implanted electronic pacemakers includes improved algorithmic processing 101. Referring to FIG. 2, the pace detection involves multiple steps including filtering at step 102, edge detection at step 104, width measurement at step 106, amplitude measurement at step 108, validating the pulse at step 110, classifying the pulse at step 112, and pace template storage at step 114. At step 102 X, Y, and Z data is filtered. The voltage samples from each channel are filtered to accentuate the pacer pulse artifacts which are roughly very narrow rectangular pulses. A 250 Hz high pass will preserve the sharp edges needed to accurately measure pulse width and the amplitude information of wider pacer pulses while rejecting many sources of interference like motion artifact and power line noise. This signal will often have a value of about zero.

At step 104, edge detection occurs. Specifically, comparison of the most recent sample to the second most recent sample (e.g., about 50 microseconds (μs) earlier) will generate a difference signal. When the absolute value of this difference exceeds a threshold an edge is detected. This threshold may be a fixed value such as 100 microvolts or it may be adjustable by the user. Preferably, it is adaptable by the software to exceed by a factor such as 100 percent a noise level estimated by the $90^{th}$ percentile of difference magnitudes in the recent one second of time. This is a leading edge if the current sample is further from the zero value than the previous sample. By convention the edge at the start of a pulse is called the leading edge. The edge at the end of a pulse is called the trailing edge.

At step 106, the width is measured. A second edge detected within a short time, approximately less than 3 milliseconds (ms) of a leading (start) edge is considered a trailing (end) edge. The difference in time between leading and trailing edges is the width of the candidate pulse. If no trailing edge is detected within the approximately 3 ms period, the previous leading edge detection is discarded.

At step 108, the amplitude is measured. The sample having the value most extreme (positive or negative) compared to zero between the leading and trailing edges determines the amplitude of the pulse.

At step 110, the pulse is validated. A valid pacer pulse may have amplitude in only one of the three channels, sometimes in only two, but usually in all three channels. The pulse is validated by measuring a distance between this pulse and several templates for pulses that are stored in a database. The timing of this pulse relative to recently validated pulses may also be checked against limits. If this pulse is too soon in time as compared to previous pulses it may be invalidated.

For example, one sophisticated function of modern pacemakers is to supply a pacing pulse to the patient at a lesser strength than previous pulses. This is a test to see if the pacemaker may reduce strength of stimulus and extend battery life. However, there is a risk that the new stimulus pulse is not of sufficient strength to stimulate the heart and so a heart beat may not result. Accordingly, the pacemaker supplies a second 'safety' pulse of the original higher strength shortly after the lower strength test pulse. This is done by the pacemaker even before the heart beat response is detected. A short while later the pacemaker determines from the timing of the heart beat response which of the first or second pacing pulses was effective. Then the pacemaker can either retain the newer lower strength setting or reject that and continue with the original strength pacing. This function may be performed only once or a few times per day but it can result in two pacing pulses very near in time to each other.

When three pacing pulses are observed in a very short period of time, it is likely that one of them is an artifact from something other than the pacer. Judging by the three axis (X,Y,Z) magnitudes and comparison to saved templates it is possible to compute which of the three pulses is most unlike any previous pulses. This pulse can then be rejected.

At step 112, the pulse is classified. If a pulse is validated it may be classified as best matching one of the templates stored in the database. These templates may be classified as right atrial stimulus, left atrial stimulus, right ventricular stimulus, or left ventricular stimulus. The classification is based on the electrical axis of the stimulus (amplitude in X, Y, and Z channels) and on the relationship of the pulses to each other and to the atrial and ventricular response of the heart.

At step 114, the pace template is stored. These templates retain information relating to a history of recent pace spike observations. The information consists primarily of amplitude in 3 channels (X,Y, Z) and the pulse width. There may be four or more templates. As newly observed pulses are matched to the templates, the templates are updated. Pulse observations that fail to match existing templates will force the creation of new templates. The few initial pulses matching a new template may be considered unusual and artificial and may be invalidated. When a sufficient count of pulses have matched a new template, the new template may be classified as non-artificial and future pulses matching it will be validated.

The cluster analysis is performed to group pacer pulse observations in categories useful to the cardiologist. Because a pacemaker, implanted or external, may be configured to stimulate possibly all four chambers of the heart, there may be up to four stimulus artifacts to detect during a single heart beat. In practice, the number is more likely to be two pulses.

Stimulation of an atria and then a ventricle is known as AV pacing and has been available for many years. Discrimination of these two pulses could be done by timing alone since the atrial stimulus results in a P-wave in the electrocardiogram (ECG) and the ventricular stimulus results in a QRS wave in the ECG and an atrial stimulus always precedes the ventricular stimulus when both are used in the same heart beat. However, sometimes a pacemaker is configured to provide the atrial pulse only when needed and the ventricular pulse only when needed. Such a pacemaker for some heart beats may only supply one of the two pulses. It becomes more difficult then to determine which pulse was supplied. In the case where the heart may fail to respond to the pacemaker so that the stimulus pulse appears without the ECG P-wave or QRS wave responses, then it may be nearly impossible to determine which pacemaker stimulus was supplied.

In very recent years pacemakers have been used to stimulate both ventricles for congestive heart failure patients. This is known as resynchronization therapy. In this case the two stimulus artifacts may be much closer in time to each other then the atrial and ventricular pulses of the AV pacing described above.

Wherever a pacing lead is implanted it causes a stimulus current to flow in a certain path during the pulse resulting in a projection of that voltage onto the patient's body surface in a pattern where more voltage appears in some locations than others. The pattern will be different for the different locations where the pacemaker stimulus contacts the heart. But for each location the pattern of subsequent stimuli will be similar. So this pattern can be used to group pacing stimuli into categories according to where the stimulus is given in the heart.

In the following table, a pulse was detected with a width of 100 μs and an amplitude in ECG lead X of 10 units and amplitude in lead Y of 30 units and 20 units in lead Z. Another pulse was detected shortly after with amplitudes 50, 62, and 5 units in leads X, Y, and Z and a width of 120 μs. After a longer period two more pulses were detected with characteristics reported in the $3^{rd}$ and $4^{th}$ rows of table 1. Cluster analysis enables all six pluses to be grouped into two categories. Timing and direction rules are useful to identify the interpretation of the pulses as atrial or ventricular, right or left chambers. In other applications it is sufficient to classify some pulses as non-pacer artifacts and others as recurring pacer pulses.

TABLE 1

Pace pulse observations, magnitude and width

| X | Y | Z | width |
|---|---|---|---|
| 10 | 30 | 20 | 100 |
| 50 | 62 | 5 | 120 |
| 11 | 29 | 19 | 101 |
| 47 | 58 | 6 | 120 |
| 9 | 30 | 21 | 100 |
| 50 | 59 | 7 | 121 |

Figure 3:
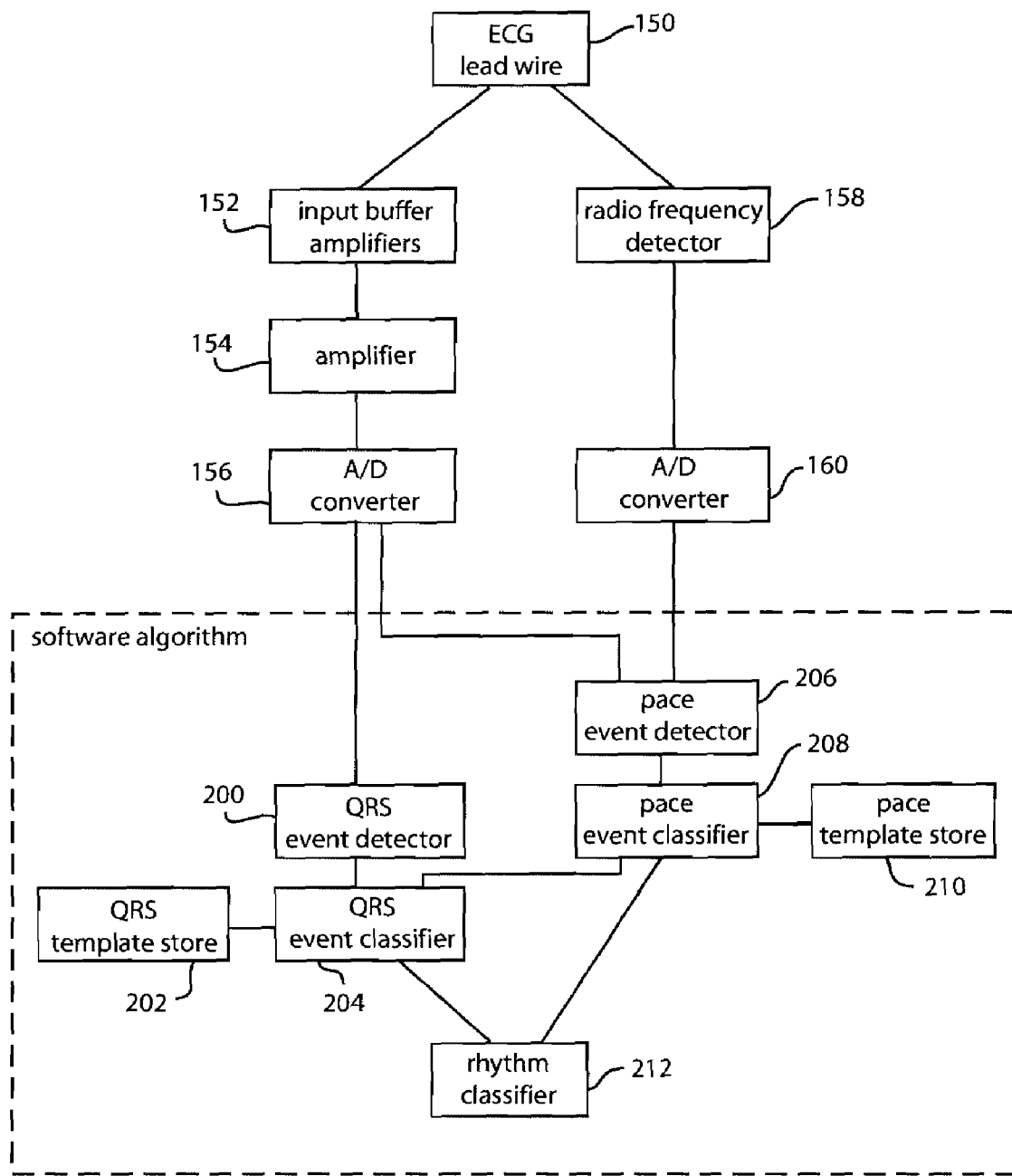
FIG. 3 is a schematic representation of a monitoring system according to an exemplary embodiment.

Referring to FIG. 3, ECG lead wire 150 connects an instrument to ECG electrodes applied to a patient's body surface according to generally acceptable standard placement locations used for electrocardiography. Multiple lead wires are actually used to convey multiple (preferably at least three quasi orthogonal) channels of ECG voltages to the input buffer amplifiers 152. As used in this disclosure, quasi orthogonal generally means that the channels are minimally aligned with each other so that the instrument may be sensitive to a pacing electrical vector in any direction of X, Y, Z space. According to an exemplary embodiment, a suitable choice of quasi orthogonal standard ECG channels may be leads II (inferior), V1 (anterior), and V5 (lateral).

Alternative sets of quasi orthogonal ECG leads are desirable in the event of loss of electrodes during monitoring or when different patient cables are used and fewer electrodes are available. A multiplexor in the circuit can be configured as needed to connect the appropriate ECG channels to the X, Y, and Z pace artifact processing channels. Table 2 describes the preferred connections for four different patient cables. The patient cable is identified by the number of electrodes it connects to the monitor. A usable alternative is a connection that might be used when one of the preferred electrodes for that cable is no longer available. For example if the patient cable has at least six or ten electrode connections, it is preferred to use ECG leads V5, II, and V1 for X, Y, and Z inputs to the pace artifact processing. However, if the V1 electrode pops off accidentally it is a usable alternative to reconfigure the multiplexor so that the X channel is redirected to ECG lead V6 and the Z channel is redirected to ECG lead V3. This redirection may not be possible with the six electrode cable because electrodes V6 and V3 are not present. However, for the six electrode cable two other configurations are usable if those electrodes are still functioning.

TABLE 2

Preferred and optional lead sets for specified patient cables

| Pace Processing Channels | | | Patient Cable Electrode Connection Count | | | |
|---|---|---|---|---|---|---|
| X | Y | Z | 3 | 5 | 6 | 10 |
| I | II | III | Preferred | Usable | Usable | Usable |
| I | II | V1 | — | Preferred | Usable | Usable |
| V5 | II | V1 | — | — | Preferred | Preferred |
| V6 | II | V3 | — | — | — | Usable |

The input buffer amplifiers 152 are generally for increased input impedance of the instrument and to minimize leakage currents into the patient. The three channels are further processed by filtering amplifiers 154 having sufficient high frequency response to preserve the important characteristics of the pacing artifacts. According to a preferred embodiment, amplifiers 154 have a frequency response in the range of about 0.05 to 10 KHz. The signal, analog up to this point, is digitized by an analog to digital converter, shown as A/D converter 156 at a high rate to sufficiently represent the short duration pacing artifacts. According to a preferred embodiment, A/D converter 156 digitizes the signal at least at about 20,000 samples per second (sps), but preferably at about 100,000 sps.

The digital data stream is then passed to the software algorithm and utilized for two purposes, QRS detection and Pace detection. The QRS event detector 200 may be of a type that generally uses strategies of further bandpass filters, adapting thresholds, and correlation to previously detected QRS shapes. These shapes are stored in the QRS template store 202. The QRS event classifier 204 uses rules to differentiate normal QRS shapes from ventricular QRS shapes from paced QRS shapes. These rules rely on the recognition of pacing artifacts at expected time relationships to the QRS detections.

Returning to the ECG lead wires, an antenna or other suitable transducer may be combined with one special electrode or special lead wire to sense the radio-frequency artifact (electric, magnetic, or both) resulting from the current flow within the patient's body during the pacemaker stimulus. This information is conveyed to a radio frequency detector 158 which may be sampled by A/D converter 160. A/D converter 160 preferably converts the samples at a rate of about 500 samples per second. This digital information is presented to the software algorithm, particularly the pace event detector 206. Pace event detector 206 uses techniques (e.g., detect edge 104, measure width 106, etc. as shown in FIG. 2) to recognize a voltage pulse in the 20,000 to 100,000 samples per second data or the pulse of RF detected energy in the 500 samples per second data. These techniques utilize a pace template store 210 and a clustering algorithm within a pace event classifier 208 in order to group recognized pacing artifacts into categories such as atrial stimulus, right ventricular stimulus, or left ventricular stimulus. The distribution of the magnitude of the pacing artifact in the three quasi orthogonal channels is a main discriminating characteristic. With information about QRS classification and pace stimulus classification it is possible for the rhythm classifier 212 to determine whether the patient is being paced, and if so, which of many types of pacing therapies is currently being given.

Figure 4:
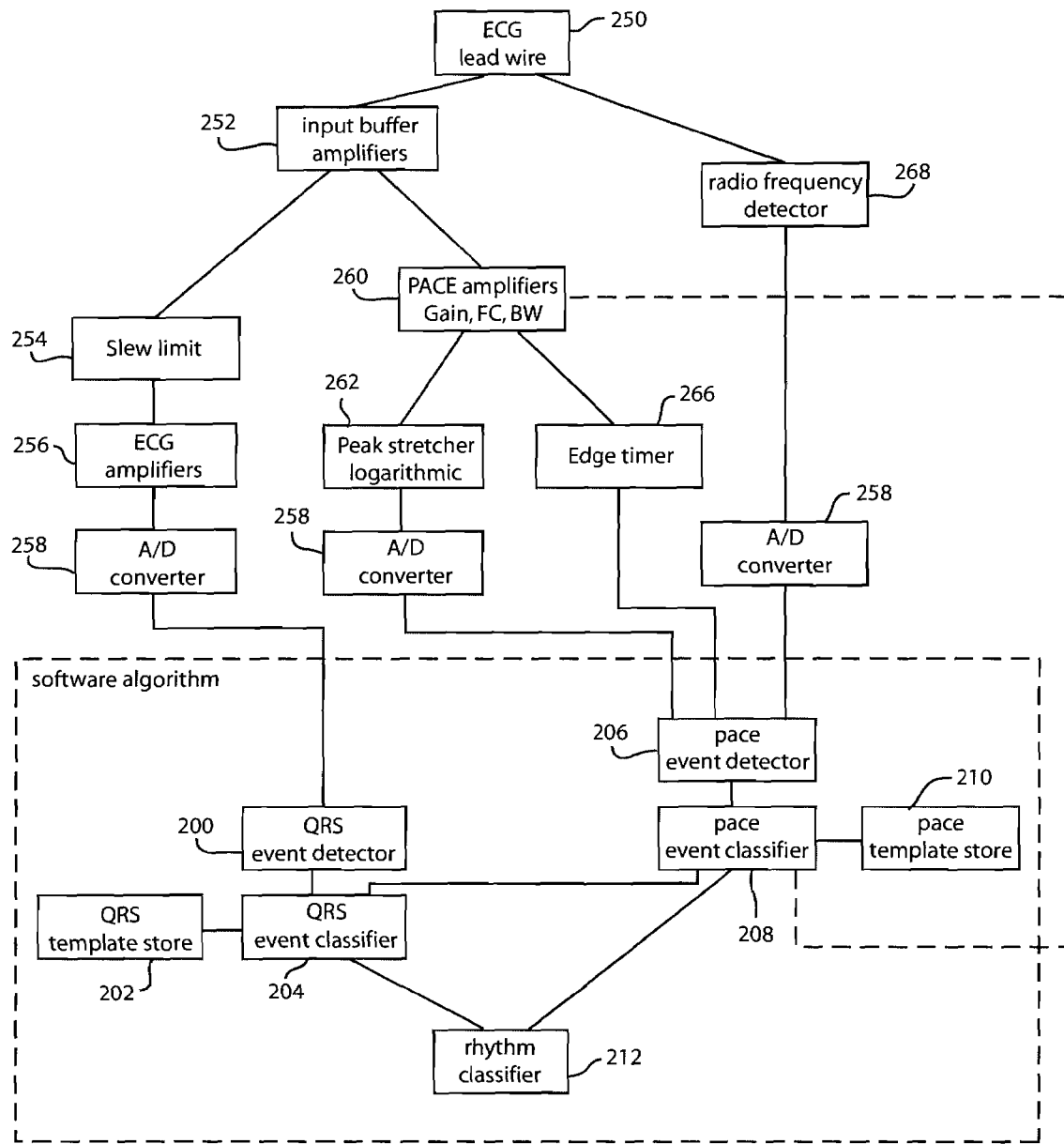
FIG. 4 is a schematic representation of a monitoring system according to an exemplary embodiment.

The embodiment illustrated in FIG. 4 differs from the embodiment of FIG. 3 in several ways. The example illustrated in FIG. 3 uses a higher sample rate A/D conversion for the ECG voltage signal and more pattern recognition in the software than the first embodiment of FIG. 4. The embodiment of FIG. 3 is designed for an instrument containing an auxiliary digital signal processor. FIG. 4 shows the same analog circuitry for the radio frequency data (as shown in FIG. 3), but a split path for the voltage data and a lower sample rate ultimately going into the software algorithm. FIG. 4 shows an embodiment where a high speed auxiliary digital signal processor is not utilized and all software executes on a more general purpose microprocessor. The split voltage signal processing begins after being sent through the input buffer amplifiers 252. One path for the heart beat signal utilizes a slew limit circuit 254 to exclude the pace artifact from this path. Slew limit circuit 254 operates in a range of about 200 to about 400 mV/seconds, preferably at about 300 mV/second. ECG amplifiers 256 need less of a high frequency response because the pacing artifact has been removed. ECG amplifiers 256 operate in a range of about 0.025 to about 300 Hz, preferably from about 0.05 to about 150 Hz. An A/D converter 258 is used for digitizing a diagnostic quality ECG signal without pacer artifacts. A/D converter 258 operates in a range of about 400 to about 600 samples per second, preferably about 500 samples per second (sps).

The second path of the voltage signal processing begins with specialized PACE amplifiers 260 for the PACE signal (e.g., PACE amplifiers Gain, center frequency, band width, etc.). These are analog circuit amplifiers, again in three quasi orthogonal channels (although only one channel is depicted in the figure). Using generally known techniques these amplifiers may be controlled (dotted line) to have adjustable gain, center frequency (FC) and band width (BW). In this way the amplifiers can be adapted over time to optimize the filtering for the pacer stimulus. The output of the programmable filter amplifier is then sent into the peak stretcher 262 (shown as peak stretcher logarithmic) which may preferably have a logarithmic amplitude response. Precise representation of the pacer stimulus magnitude is less important than its distribution in the three quasi orthogonal channels. Because the possible stimulus magnitudes span a very wide dynamic range (very small artifacts to very large artifacts) it is useful to contract the dynamic range by a logarithm function so that the subsequent A/D converter 258 (at 500 sps) may not require such a wide code word (e.g., a fewer number of bits in the digital code). This logarithm function means that small artifacts will be adequately represented in the three channels while very large artifacts can also be adequately represented. The edge timer circuit 266, by processing in the analog domain, may have time precision much increased compared to what the software algorithm could otherwise determine from the 500 sps data which has 2 millisecond gaps between samples.

Returning to the ECG lead wires, an antenna or other suitable transducer may be combined with one special electrode or special lead wire to sense the radio-frequency artifact resulting from the current flow within the patient's body during the pacemaker stimulus. This information is conveyed to a radio frequency detector 268 which may be sampled by A/D converter 258. A/D converter 258 preferably converts the samples at a rate of about 500 samples per second. This digital information is presented to the software algorithm, particularly the pace event detector 206. The algorithm may be the same or similar to that shown and described in FIG. 3.

It is important to note that the above-described preferred embodiments are illustrative only. Although the invention has been described in conjunction with specific embodiments thereof, those skilled in the art will appreciate that numerous modifications are possible without materially departing from the novel teachings and advantages of the subject matter described herein. Accordingly, these and all other such modifications are intended to be included within the scope of the present invention as defined in the appended claims. The order or sequence of any process or method steps may be varied or re-sequenced according to alternative embodiments. In the claims, any means-plus-function clause is intended to cover the structures described herein as performing the recited function and not only structural equivalents but also equivalent structures. Other substitutions, modifications, changes and omissions may be made in the design, operating conditions and arrangements of the preferred and other exemplary embodiments without departing from the spirit of the present invention.

What is claimed is:

1. A method of monitoring signals form an implantable medical device that provides a stimulus to a patient comprising:
    detecting a radio frequency artifact from implantable medical device; and
    processing the radio frequency artifact from the implantable medical device in order to determine where artifact occurs in an ECG and identify heartbeats that are paced and heartbeats that are paced and heartbeats that are not paced and occurrences of pacing that fail to stimulate a heart beat.

2. The method of claim 1 further comprising excluding artifact from heart rate determinations.

3. The method of claim 1 wherein detecting the radio frequency artifact comprises using a monitor having an antenna that receives the signals.

4. The method of claim 1 wherein processing the radio frequency artifact comprises using circuitry capable of monitoring multiple channels of the signals.

5. The method of claim 4 wherein processing the voltage artifact further comprises using a slew limit to limit pace artifact energy in the signals.

6. The method of claim 4 wherein processing the voltage artifact further comprises using a tunable band pass filter to isolate the radio frequency artifact from ambient noise.

7. A monitoring method comprising:
    detecting a radio frequency artifact from signals of an implantable pacemaker;
    processing the radio frequency artifact from the signals of the implantable pacemaker;
    determining where radio frequency artifact occurs in an ECG;
    identifying heart beats that are paced and heart beats that are not paced and occurrences of pacing that fail to stimulate a heart beat;
    excluding voltage artifact from a heart rate determination.

8. The method of claim 7 further comprising classifying pacing stimuli according to heart chamber location.

9. The method of claim 7 wherein detecting the radio frequency artifact comprises using a monitor having an antenna that receives the signals.

10. The method of claim 7 wherein processing the radio frequency artifact comprises using circuitry capable of monitoring multiple channels of the signals.

11. The method of claim 7 wherein processing the voltage artifact further comprises using a slew limit to limit pace artifact energy in the signals.

12. The method of claim 10 wherein processing the voltage artifact further comprises using a tunable band pass filter to isolate the radio frequency artifact from ambient noise.

13. A method of monitoring signals form an implantable medical device that provides a stimulus to a patient comprising:
  detecting a radio frequency artifact from implantable medical device;
  processing the radio frequency artifact from the implantable medical device in order to determine where artifact occurs in an ECG and identify heartbeats that are paced and heartbeats that are paced and heartbeats that are not paced and occurrences of pacing that fail to stimulate a heart beat;
  classifying pacing stimuli according to heart chamber location; and
  excluding artifact from heart rate determinations.

14. The method of claim 13 wherein detecting the radio frequency artifact comprises using a monitor having an antenna that receives the signals.

15. The method of claim 13 wherein processing the radio frequency artifact comprises using circuitry capable of monitoring multiple channels of the signals.

16. The method of claim 15 wherein processing the voltage artifact further comprises using a slew limit to limit pace artifact energy in the signals.

17. The method of claim 15 wherein processing the voltage artifact further comprises using a tunable band pass filter to isolate the radio frequency artifact from ambient noise.

* * * * *